US008679471B2

(12) United States Patent
Carroll et al.

(10) Patent No.: US 8,679,471 B2
(45) Date of Patent: Mar. 25, 2014

(54) MODULATION OF REGULATORY T CELLS BY HUMAN IL-18

(75) Inventors: Richard G. Carroll, Lansdowne, PA (US); Xiaochuan Shan, Cherry Hill, NJ (US); Gwenn-ael Danet-Desnoyers, Philadelphia, PA (US); Carl H. June, Merion Station, PA (US)

(73) Assignee: The Trustees of the Univesity of Pennsylvania, Philadelphia, PA (US)

( * ) Notice: Subject to any disclaimer, the term of this patent is extended or adjusted under 35 U.S.C. 154(b) by 115 days.

(21) Appl. No.: 13/250,425

(22) Filed: Sep. 30, 2011

(65) Prior Publication Data

US 2012/0064033 A1 Mar. 15, 2012

Related U.S. Application Data

(63) Continuation of application No. 12/441,051, filed as application No. PCT/US2007/019995 on Sep. 14, 2007, now abandoned.

(60) Provisional application No. 60/844,521, filed on Sep. 14, 2006.

(51) Int. Cl.
*A61K 38/19* (2006.01)
*A61K 38/20* (2006.01)

(52) U.S. Cl.
USPC ... 424/85.2; 424/93.1; 424/130.1; 424/278.1; 514/19.2; 514/19.3

(58) Field of Classification Search
None
See application file for complete search history.

(56) References Cited

U.S. PATENT DOCUMENTS

| 6,893,633 | B2 | 5/2005 | Hellstrand et al. | |
|---|---|---|---|---|
| 7,776,822 | B2 * | 8/2010 | Terman | 424/184.1 |
| 2003/0143198 | A1 | 7/2003 | Johanson et al. | |
| 2005/0008615 | A1 | 1/2005 | Bam et al. | |
| 2005/0063944 | A1 | 3/2005 | Li | |
| 2007/0212328 | A1 * | 9/2007 | Bruck et al. | 424/85.2 |

FOREIGN PATENT DOCUMENTS

| EP | 1433484 | 6/2004 |
|---|---|---|
| EP | 1736169 | 12/2006 |
| WO | WO 99/22760 | 5/1999 |
| WO | WO 99/56755 | 11/1999 |
| WO | WO99/59565 | 11/1999 |
| WO | WO 01/56387 | 8/2001 |
| WO | WO 01/93898 | 12/2001 |
| WO | WO 02/083063 | 10/2002 |
| WO | WO 2004/091517 | 10/2004 |
| WO | WO 2005/077411 | 8/2005 |

OTHER PUBLICATIONS

Reddy et al., Blood 101:2877-2885, 2003.*

Powell et al., Partial Reduction of Human FOXP3+ CD4 T Cells in Vivo After CD25-Directed Recombinant Immunotoxin Administration, Journal of Immunotherapy, (Feb.-Mar. 2008) 31(2):189-98.
Office Action dated Oct. 10, 2012 issued in corresponding European application No. 07838231.4.
Shin-ichiro Kashiwamura et al, IL-18 and IL-18 Receptor, Japan Clinical Med, 56:152-60 (1998) (Translation of relevant portions and abstract provided).
Steps in Medicine, 200(13):1095-6 (2002) (Translation of relevant portions provided).
Hikoaki Fukaura et al, IL-18 in Multiple Sclerosis, Japan Clinical Med, 61:1416-21 (2003) (Translation of relevant portion and abstract provided).
Hashimoto et al, Interleukin-18 (IL-18) Activates Natural Killer (NK) Cella (sic) and Induces Tumor Apoptosis, Head and Neck Cancer, 29(1):217-23 (2003) (Translation of abstract provided).
Office Action dated Sep. 11, 2012 issued in corresponding Japanese application No. 2009-528304 (English translation only).
Andaloussi and Lesniak, An increase in CD4+CD25+FOXP3+ regulatory T cells in tumor-infiltrating lymphocytes of human glioblastoma multiforme, Neuro-Oncology, 8(3):234-43 (Jul. 2006).
Barnett et al, Regulatory T cells in ovarian cancer: biology and therapeutic potential, Cancer Immunity, 6(1):20 (Dec. 2005).
Belkaid et al, CD4+CD25+ regulatory T cells control Leishmania major persistence and immunity, Nature, 420(6915):502-7 (Dec. 2002).
Beyer et al, Reduced frequencies and suppressive function of CD4+CD25hi regulatory T cells in patients with chronic lymphocytic leukemia after therapy with fludarabine, Blood, 106(6):2018-25. Epub May 24, 2005.
Chu et al, N-benzylisatin sulfonamide analogues as potent caspase-3 inhibitors: synthesis, in vitro activity, and molecular modeling studies, J. Medicinal Chemistry, 48(24):7637-47 (Dec. 2005).
Clarke et al, CD4+CD25+FOXP3+ regulatory T cells suppress anti-tumor immune responses in patients with colorectal cancer, PLoS One, 1:e129 (Dec. 2006).
Curiel et al, Blockade of B7-H1 improves myeloid dendritic cell-mediated antitumor immunity, Nature Medicine, 9(5):562-7. Epub Apr. 21, 2003.
Dannull et al, Enhancement of vaccine-mediated antitumor immunity in cancer patients after depletion of regulatory T cells, J. Clinical Investigation, 115(12):3623-33. Epub Nov. 23, 2005.
DeLong et al, Regulatory T cells and cytokines in malignant pleural effusions secondary to mesothelioma and carcinoma, Cancer Biology & Therapy, 4(3):342-6. Epub Mar. 1, 2005.
Fontenot et al, Regulatory T cell lineage specification by the forkhead transcription factor foxp3, Immunity, 22(3):329-41 (Mar. 2005).
Fu et al, Identification of important amino acid residues for human IL-18 function by mutant construction, ACTA Biochimicha et Biophysica Sinica, 35(5):409-15 (May 2003).

(Continued)

*Primary Examiner* — Daniel C Gamett
(74) *Attorney, Agent, or Firm* — Howson & Howson, LLP

(57) ABSTRACT

The present invention relates to compositions and methods for modulating the presence and/or activity of regulatory T cells in a subject.

18 Claims, 6 Drawing Sheets

(56) References Cited

OTHER PUBLICATIONS

Giorgini et al, Blockade of chronic graft-versus-host disease by alloantigen-induced CD4+CD25+Foxp3+ regulatory T cells in nonlymphopenic hosts, J. Leukocyte Biology, 1053-61. Epub Aug. 7, 2007.

Han et al, Selective, reversible caspase-3 inhibitor is neuroprotective and reveals distinct pathways of cell death after neonatal hypoxic-ischemic brain injury, J. Biological Chemistry, 277(33):30128-36. Epub Jun. 10, 2002.

Hisaeda et al, Escape of malaria parasites from host immunity requires CD4+ CD25+ regulatory T cells, Nature Medicine, 10(1):29-30. Epub Dec. 21, 2003.

Im et al, Suppression of experimental myasthenia gravis, a B cell-mediated autoimmune disease, by blockade of IL-18, FASEB Journal, 15(12):2140-8 (Oct. 2001).

Iwashiro et al, Immunosuppression by CD4+ regulatory T cells induced by chronic retroviral infection, PNAS, 98(16):9226-30. Epub Jul. 17, 2001.

Mottet et al, CD4+CD25+Foxp3+ regulatory T cells: from basic research to potential therapeutic use, Swiss Medical Weekly, 137(45-46):625-34 (Nov. 17, 2007).

Okun et al, Screening for caspase-3 inhibitors: a new class of potent small-molecule inhibitors of caspase-3, J. Biomolecular Screening, 11(3):277-85. Epub Feb. 20, 2006.

Pages et al, Effector memory T cells, early metastasis, and survival in colorectal cancer, New England J. Medicine, 353(25):2654-66 (Dec. 2005).

Pages et al, Modulation of interleukin-18 expression in human colon carcinoma: consequences for tumor immune surveillance, International J. Cancer, 84(3):326-30 (Jun. 1999).

Pandiyan et al, The control of CD4+CD25+Foxp3+ regulatory T cell survival, Biology Direct, 3:6 (Feb. 2008).

Reddy et al, Interleukin-18: recent advances, Current Opinion in Hematology, 11(6):405-10 (Nov. 2004).

Sakaguchi et al, Foxp3+ CD25+ CD4+ natural regulatory T cells in dominant self-tolerance and autoimmune disease, Immunological Reviews, 212(1):8-27 (Aug. 2006).

Sakaguchi et al, Naturally arising Foxp3-expressing CD25+CD4+ regulatory T cells in self-tolerance and autoimmune disease, Current Topics in Microbiology and Immunology, 305:51-66 (2006).

Sakaguchi, Regulatory T cells: meden agan, Immunological Reviews, 212(1):5-7 (Aug. 2006).

Taylor et al, Removal of regulatory T cell activity reverses hyporesponsiveness and leads to filarial parasite clearance in vivo, 174(8):4924-33 (Apr. 2005).

Wolf et al, Regulatory T cells in cancer biology: a possible new target for biochemical therapies, Mini Reviews in Medicinal Chemistry, 6(5):509-13 (May 2006).

Wolf et al, The expression of the regulatory T cell-specific forkhead box transcription factor FoxP3 is associated with poor prognosis in ovarian cancer, Clinical Cancer Research, 11(23):8326-31 (Dec. 2005).

Woo et al, Cutting edge: Regulatory T cells from lung cancer patients directly inhibit autologous T cell proliferation, 168(9):4272-6 (May 2002).

Zhang et al, Intratumoral T cells, recurrence, and survival in epithelial ovarian cancer, New England J. Medicine, 348(3):203-13 (Jan. 2003).

Born et al, Cloning of a Novel Receptor Subunit, AcPL, Required for Interleukin-18 Signaling, Journal of Biological Chemistry, 2873(45):29445-29450, Nov. 1998.

Ghayer et al, Caspase-1 Processes IFN-gamma-inducing Factor and Regulates LPS-induced IFN-gamma Production, Nature, 386(6625):619-623, Apr. 1997.

Gracie et al, Interleukin-18, Journal Leukocyte Biology, 73(2):213-224, Feb. 2003.

Gu et al, Activation of Interferon-gamma Inducing Factor Mediated by Interleukin-1beta Converting Enzyme, Science, 275(5297):206-209, Jan. 1997.

Nakanishi et al, Interleukin-18 is a Unique Cytokine that Stimulates Both Th1 and Th2 Responses Depending on its Cytokine Milieu, Cytokine Growth Factor Reviews, 12(1):53-72, Mar. 2001.

Nakanishi et al, Interleukin-18 Regulates Both Th1 and Th2 Responses, Annual Reviews Immunology, 19:423-474, Apr. 2001.

Novick et al, Interleukin-18 Binding Protein: a Novel Modulator of the Th1 Cytokine Response, Immunity, 10(1):127-136, Jan. 1999.

Sakaguchi et al, Immunologic Self-Tolerance Maintained by Activated T Cells Expressing IL-2 Receptor Alpha-Chains (CD25). Breakdown of a Single Mechanism of Self-Tolerance Causes Various Autoimmune Diseases, Journal of Immunology, 155(3):1151-1164, Aug. 1995.

Thornton et al, CD4+CD25+ Immunoregulatory T Cells Suppress Polyclonal T Cell Activation in Vitro by Inhibiting Interleukin 2 Production, Journal of Experimental Medicine, 188(2):287-296, Jul. 1998.

Torigoe et al, Purification and Characterization of the Human Interleukin-18 Receptor, Journal of Biological Chemistry, 272(41):25737-25742, Oct. 1997.

Woo et al, Cutting Edge: Regulatory T Cells From Lung Cancer Patients Directly Inhibit Autologous T Cell Proliferation, Journal Immunology, 168(9):4272-4276, May 2002.

International Preliminary Report on Patentability dated Mar. 17, 2009 issued in corresponding international patent application No. PCT/US2007/019995.

International Search Report dated May 21, 2008 issued in corresponding international patent application No. PCT/US2007/019995.

Communication dated Aug. 12, 2011 issued in corresponding EP patent application No. 07838231.4 including extended search report and opinion.

Office Action dated Mar. 30, 2011 issued in U.S. Appl. No. 12/441,051.

Curiel, T. Tregs and rethinking cancer immunotherapy, Journal of Clinical Investigation, (May 2007) 117(5):1167-1174.

Barnett et al. 2005. Depleting regulatory T cells is associated with improved immunity and tumor clearance in human cancer. 625.

Powell Jr, D.J. et al. 2007. Inability to mediate prolonged reduction of regulatory T Cells after transfer of autologous CD25-depleted PBMC and interleukin-2 after lymphodepleting chemotherapy. J. Immunother, (1997) 30:438-447.

Powell Jr, D.J. et al. 2007. Administration of a CD25-directed immunotoxin, LMB-2, to patients with metastatic melanoma induces a selective partial reduction in regulatory T cells in vivo. The Journal of Immunology 179:4919.

* cited by examiner

SEQUENCE LISTING

<160> NUMBER OF SEQ ID NOS: 4

<210> SEQ ID NO 1
<211> LENGTH: 157

```
<212> TYPE: PRT
<213> ORGANISM: Homo sapiens

<400> SEQUENCE: 1

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Glu Asp Glu Leu
            130                 135                 140

Gly Asp Arg Ser Ile Met Phe Thr Val Gln Asn Glu Asp
145                 150                 155

<210> SEQ ID NO 2
<211> LENGTH: 471
<212> TYPE: DNA
<213> ORGANISM: Homo sapiens

<400> SEQUENCE: 2
tactttggca agcttgaatc taaattatca gtcataagaa atttgaatga ccaagttctc        60
ttcattgacc aaggaaatcg gcctctattt gaagatatga ctgattctga ctgtagagat       120
aatgcacccc ggaccatatt tattataagt atgtataaag atagccagcc tagaggtatg       180
gctgtaacta tctctgtgaa gtgtgagaaa atttcaactc tctcctgtga gaacaaaatt       240
atttccttta aggaaatgaa tcctcctgat aacatcaagg atacaaaaag tgacatcata       300
ttctttcaga gaagtgtccc aggacatgat aataagatgc aatttgaatc ttcatcatac       360
gaaggatact tctagcttg tgaaaaagag agagaccttt ttaaactcat tttgaaaaaa       420
gaggatgaat gggggatag atctataatg ttcactgttc aaaacgaaga c                  471

<210> SEQ ID NO 3
<211> LENGTH: 157
<212> TYPE: PRT
<213> ORGANISM: Mus musculus

<400> SEQUENCE: 3

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
```

-continued

```
                65                  70                  75                  80

Ser Phe Glu Glu Met Asp Pro Pro Glu Asn Ile Asp Asp Ile Gln Ser
                    85                  90                  95

Asp Leu Ile Phe Phe Gln Lys Arg Val Pro Gly His Asn Lys Met Glu
                100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Lys Asp Glu Asn Gly Asp
        130                 135                 140

Lys Ser Val Met Phe Thr Leu Thr Asn Leu His Gln Ser
145                 150                 155

<210> SEQ ID NO 4
<211> LENGTH: 471
<212> TYPE: DNA
<213> ORGANISM: Mus musculus

<400> SEQUENCE: 4
aactttggcc gacttcactg tacaaccgca gtaatacgga atataaatga ccaagttctc     60
ttcgttgaca aaagacagcc tgtgttcgag gatatgactg atattgatca aagtgccagt    120
gaaccccaga ccagactgat aatatacatg tacaaagaca gtgaagtaag aggactggct    180
gtgaccctct ctgtgaagga tagtaaaatg tctaccctct cctgtaagaa caagatcatt    240
tcctttgagg aaatggatcc acctgaaaat attgatgata tacaaagtga tctcatattc    300
tttcagaaac gtgttccagg acacaacaag atggagtttg aatcttcact gtatgaagga    360
cactttcttg cttgccaaaa ggaagatgat gctttcaaac tcattctgaa aaaaaaggat    420
gaaaatgggg ataaatctgt aatgttcact ctcactaact tacatcaaag t             471
```

MODULATION OF REGULATORY T CELLS BY HUMAN IL-18

CROSS-REFERENCE TO RELATED APPLICATIONS

This application is a continuation of U.S. patent application Ser. No. 12/441,051 filed Oct. 30, 2009, which is a National Stage application of International Patent Application No. PCT/US2007/019995, filed Sep. 14, 2007, which in turn claims the benefit pursuant to 35 U.S.C. §119(e) of U.S. Provisional Application No. 60/844,521, filed on Sep. 14, 2006, which applications are hereby incorporated by reference in their entirety herein.

BACKGROUND OF THE INVENTION

Interleukin-18 (IL-18) is a potent cytokine that plays roles in both innate and acquired immune responses (Nakanishi et al., 2001, Cytokine Growth Factor Rev. 12(1):53-72; Nakanishi et al., 2001, Annu. Rev. Immunol. 19:423-74; Gracie et al., 2003, J. Leukoc. Biol. 73(2):213-224; Reddy, 2004, Curr. Opin. Hematol. 1(6):405-410). IL-18 expression plays a role in a wide variety of pathologic conditions, including autoimmune diseases, bacterial and viral infections, and cancer. Biological activities of IL-18 include induction of interferon-γ (IFN-γ) by, for instance, T cells and splenocytes, enhancement of the killing activity of natural killer cells (NKTs) and helping induce differentiation of naïve CD4+ T cells to type 1 effector T cells (Th1).

IL-18 is synthesized as a biologically-inactive precursor polypeptide. Processing by caspase-1, which cleaves off the leader sequence, yields the biologically-active form (Ghayer et al., 1997, Nature 386:619-623; Gu et al., 1997, Science 275(5297):206-209). Active human IL-18 contains 157 amino acids. IL-18 receptor (IL-18R) components, IL-18Rα and IL-18Rβ, have been identified (Torigoe et al., 1997, J. Biol. Chem. 272:25737-25742; Born et al., 1998, J. Biol. Chem. 2873:29445-29450). A naturally-occurring soluble inhibitor of IL-18, dubbed IL-18BP, has also been identified, which inhibits IL-18 activity by binding to IL-18 (Novick et al., 1999, Immunity 10:127-136).

T cells play a critical role in immune responses. Regulatory T cells (Tregs), are a distinct population of T lymphocytes that have the capacity to dominantly suppress the proliferation of responder T cells in vitro and inhibit autoimmune disease in vivo (Sakaguchi et al., 1995, J. Immunol. 155:1151-1164; Sakaguchi et al., 2006, Curr. Top. Microbiol. Immunol. 305: 51-66; Thornton et al., 1998, J. Exp. Med. 188:287-296). Tregs, originally identified as a CD4$^+$CD25' cell population, are also characterized by the expression of the forkhead family transcription factor FoxP3 (Fontenot et al., 2005, Immunity 22:329-341).

Tumors express tumor-associated antigens, which should result in a immune reaction. However, such tumor-associated antigen specific immune responses have not typically been observed. Tregs have been implicated as major contributors to the ultimate failure of anti-tumor immune responses in humans (Wolf et al., 2006, Mini Rev. Med. Chem. 6(5): 509513). For instance, in ovarian cancer, Tregs suppress tumor-specific T cells and high numbers of tumor-associated Tregs are associated with reduced survival time (Curiel et al., 2003, Nat. Med. 9:562-567; Wolf et al., 2005, Clin. Cancer Res. 11:8326-8331; Curiel et al., 2006, Meeting Abstract, Can. Immunity 6 Suppl. 1, p. 20). Furthermore, an increased number of intratumoral effector T cells in ovarian cancer has been associated with a better prognosis (Zhang et al., 2003, N. Engl. J. Med. 348:203-213). A similar observation has been made with respect to colorectal cancer (Pages et al., 2005, N. Engl. J. Med. 353:2654-2666). Lung tumors have been shown to have a high number of Tregs, and the evidence suggests that Tregs selectively inhibit the host immune response and may thereby contribute to cancer progression (Woo et al., 2002, J. Immunol. 168:4272-4276). Tregs have also been shown to be elevated in tumor samples from glioblastoma multiforme patients (Andaloussi et al., 2006, Neuro-oncol. 8:234-243).

Administration of DAB$_{389}$IL-2, a recombinant IL-2 diphtheria toxin conjugate, to eliminate Tregs from peripheral blood of metastatic renal cell carcinoma patients prior to vaccination with tumor RNA-transfected dendritic cells resulted in enhanced stimulation of tumor-specific T cells (Dannull et al., 2005, J. Clin. Inves. 115:3623:3633). Disadvantageously, DAB$_{389}$IL-2 removes activated T cells and therefore, cannot be used following vaccination. Fludarabine has been shown to either eliminate or block Tregs in chronic lymphocytic leukemia patients (Beyer et al., 2005, Blood 106:2018-2025). Disadvantageously, fludarabine can cause suppression of bone marrow cells and neurotoxicity.

Tregs also play a role in some viral and parasitic infections. For instance, an overabundance of Tregs and resultant immune suppression have been detected in retroviral infections (Iwashiro et al., 2001, PNAS 98:9226-9230). Immune suppression by Tregs has also been found in *Leishmania* and malaria mouse models (Belkaid et al., Nature 420:502; Hisaeda et al., 2004, Nat. Med. 10:29). In a filarial-infected mouse model, reduction in the number of Tregs by antibody therapy resulted in a dramatic reduction in parasite numbers (Taylor et al., 2005, J. Immunol. 174:4924-4933).

Thus, it is clear there is a need in the art for a new method for inhibiting or reducing Tregs in the treatment of cancer and other diseases involving Tregs. The present invention satisfies this need.

BRIEF SUMMARY OF THE INVENTION

The invention features a method for decreasing the number of CD4$^+$CD25$^+$FoxP3$^+$ Tregs in a subject, the method comprising the step of administering a therapeutically-effective amount of interleukin 18 (IL-18) to the subject, wherein the CD4$^+$ CD25$^+$ FoxP3$^+$ Tregs are selectively depleted. In one embodiment, the subject is afflicted with at least one disorder selected from cancer, a retroviral infection or a parasitic infection.

The invention also features a method for decreasing the number of systemic Treg cells in a subject afflicted with cancer, the method comprising the step of administering a therapeutically-effective amount of IL-18 to the subject.

Also provided by the invention is a method for decreasing the number of intratumoral Treg cells in a subject afflicted with cancer, the method comprising the step of administering a therapeutically-effective amount of IL-18 to the subject.

A method for increasing the number of systemic CD8$^+$ effector T-cells in a subject afflicted with cancer, the method comprising the step of administering a therapeutically-effective amount of IL-18 to the subject is also provided by the invention.

The invention also provides a method for increasing the number of intratumoral CD8$^+$ effector T-cells in a subject afflicted with cancer, the method comprising the step of administering a therapeutically-effective amount of IL-18 to the subject.

In some embodiments, the IL-18 is human IL-18. In some embodiments, the IL-18 is conjugated to polyethylene glycol. In some embodiments, the subject is a human subject. In some embodiments, the IL-18 is administered in conjunction with at least one additional therapeutic component. In some embodiments, the additional therapeutic component is an antibody, an antibody-toxin conjugate, a toxin, a chemotherapeutic molecule, a DNA vaccine, an antisense molecule, an siRNA molecule, a stem cell, a tumor-specific T cell, or an antigen-presenting cell.

In some embodiments, the IL-18 is administered as part of an allogeneic tissue transplant. In some embodiments, the tissue transplant is selected from peripheral blood mononuclear cell (PBMC) transplant or bone marrow transplant (BMT).

In some embodiments, the cancer is lung cancer, gastrointestinal cancer, genitourinary tract cancer, liver cancer, bone cancer, nervous system cancer, gynecological cancer, breast cancer, hematologic cancer, skin cancer, or adrenal gland cancers.

The invention further provides a method for depleting $CD4^+CD25^+FoxP3^+$ Tregs in a subject, the method comprising the step of administering a composition to the subject, wherein the composition increases the activity of IL-18 in the subject, wherein the $CD4^+CD25^+FoxP3^+$ Tregs are selectively depleted.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 2A and 2B, is a series of graphs depicting the number of Tregs as a result of IL-18 treatment of tumor-bearing $\beta$2-microglobulin$^{-/-}$/NOD/scid mice. FIG. 2A depicts the results of immunohistochemistry on sections of spleen. FIG. 2B depicts the results of immunohistochemistry on sections of tumor. Antibody-reactive cells per 400× field were enumerated blindly. Solid bars depict sections from IL-18-treated animals, while open bars represent sections from mock-IL-18-treated animals.

DETAILED DESCRIPTION

Figure 1:
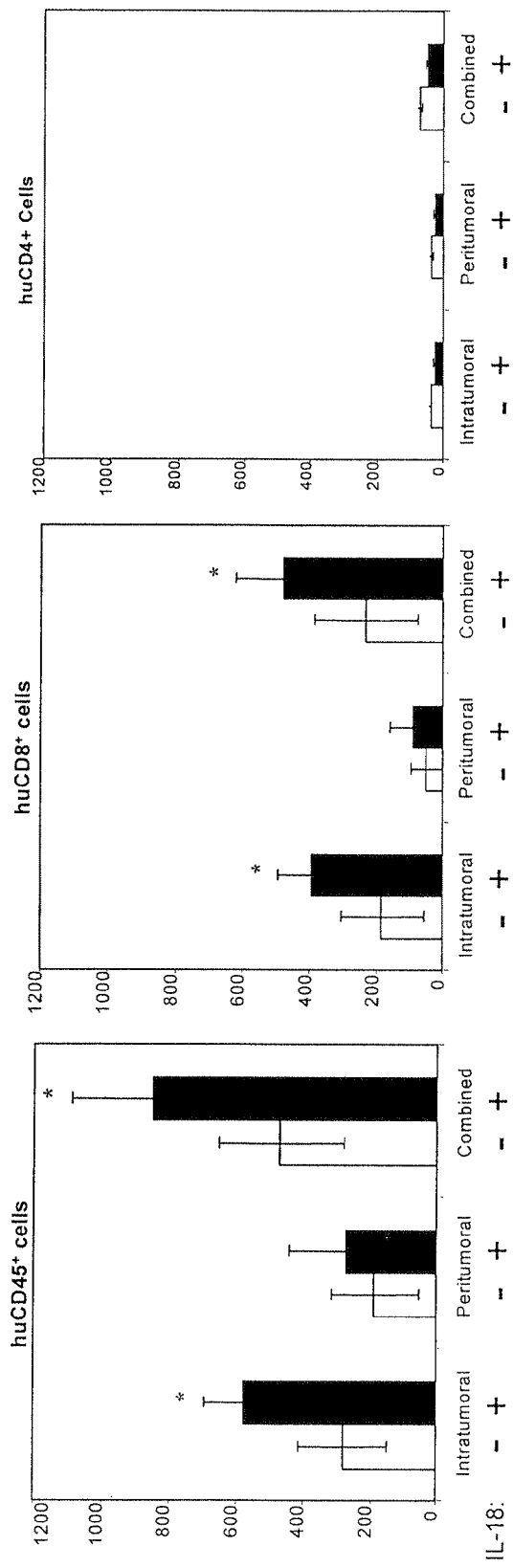
FIG. 1 is a series of graphs depicting, in the presence and absence of rhIL-18 treatment, tumor infiltration by human T cells in a mouse human tumor xenograft model, as described in Experimental Example 1. Paraffin sections were reacted with antibody specific for human CD45 (left panel), CD8 (middle panel), or CD4 (right panel). Antibody-reactive cells per 100× field were enumerated blindly and assigned as being either intra- or peri-tumoral in location. Solid bars depict results from IL-18 treated animals. Open bars depict results from mock-treated animals. Asterisks indicate significant differences ($p<0.05$) between rhIL-18-treated and untreated specimens, as measured by a T test for paired two-sample means.

The present invention relates in part to the discovery that administration of IL-18 exerts differential effects on engraftment of human T cell subsets. The present disclosure demonstrates that administration of human IL-18 in a human lung cancer xenograft mouse model treated with allogeneic PMBCs results in a significantly decreased number of Tregs intratumorally. Additionally, there is also a systemic decrease in Tregs as a result of IL-18 administration. Furthermore, IL-18 administration has very little effect on overall $CD4^+$ T cell engraftment. The present disclosure also demonstrates that IL-18 administration promotes $CD8^+$ T cell engraftment, both intratumorally and systemically. These IL-18-induced effects are also observed in the absence of tumors. As such, the present invention includes methods of decreasing the number of Tregs in a subject and methods of increasing $CD8^+$ cells in a subject.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, a "disease" is a state of health of an animal wherein the animal cannot maintain homeostasis, and wherein, if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a disease or disorder is "alleviated" if the severity of a symptom of the disease or disorder, the frequency with which such a symptom is experienced by a patient, or both, are reduced.

As used herein, a "therapeutically effective amount" refers to a nontoxic but sufficient amount of an agent to provide the desired biological result. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "therapeutic" treatment is a treatment administered to a subject who exhibits signs of pathology for the purpose of diminishing or eliminating those signs.

A "subject" of diagnosis or treatment is a mammal, including a human. Non-human animals subject to diagnosis or treatment in the methods of the invention include, for example, primates, cattle, goats, sheep, horses, dogs, cats, mice, rats, and the like.

"Graft," as used herein, refers to any free (unattached) cell, tissue or organ for transplantation.

"Allograft," as used herein, refers to a transplanted cell, tissue or organ derived from a different animal of the same species than the transplant recipient.

"Xenograft," as used herein, refers to a transplanted cell, tissue or organ derived from an animal of a different species than the transplant recipient.

As used herein, "tissue transplant" refers to the transplant of any tissue into a subject. Tissues that may be transplanted include, but are not limited to, peripheral blood mononuclear cells (PBMCs), bone marrow, stem cells, and organs, or portions thereof, including, but not limited to skin, liver, kidney, lung, heart, pancreas, eyes, corneas, heart valves, bone, intestine, vein and arteries.

As used here, "intratumoral," as it refers to a T cell located within tumor cell islets (i.e. juxtaposed to clearly malignant epithelial cells), while peritumoral T cells are located in the stroma that surrounds and infiltrates a tumor. Thus, a T cell may be located within the tumor, but by virtue of being intimately associated with stromal rather than actual malignant cells, it may not be viewed as an intratumoral T cell. Any method known in the art for detecting a T cell that preserves the tumor architecture may be used to ascertain if it is intratumoral. A non-limiting example is the use of immunohistochemical detection methods on a pathology tissue sample.

"Polypeptide," as used herein, refers to a polymer composed of amino acid residues, related naturally-occurring structural variants, and synthetic non-naturally-occurring variants thereof, linked via peptide bonds. Synthetic polypeptides can be synthesized, for example, using an automated polypeptide synthesizer.

The term "protein" typically refers to large polypeptides.

The term "peptide" typically refers to short polypeptides. Conventional notation is used herein to portray polypeptide sequences: the left-hand end of a polypeptide sequence is the amino-terminus (N-terminus); the right-hand end of a polypeptide sequence is the carboxyl-terminus (C-terminus).

The term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by column chromatography, gel electrophoresis or HPLC analysis. A compound, e.g., a protein, is also substantially purified when it is essentially free of naturally associated components or when it is separated from the native contaminants which accompany it in its natural state.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, "recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

As used herein, a "recombinant polypeptide" is one which is produced upon expression of a recombinant polynucleotide.

A "vector" is a composition of matter which comprises an isolated nucleic acid and which can be used to deliver the isolated nucleic acid to the interior of a cell.

As used herein, an "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors useful in the invention include all those known in the art, such as cosmids, plasmids (e.g., naked or contained in liposomes) and viruses that incorporate the recombinant polynucleotide.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A host cell that comprises a recombinant polynucleotide is referred to herein as a "recombinant host cell." A gene that is expressed in a recombinant host cell, wherein the gene comprises a recombinant polynucleotide, produces a recombinant polypeptide.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal peptide is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

A "receptor" is a compound that specifically binds to a ligand.

A "ligand" is a compound that specifically binds to a target receptor.

For instance, IL-18 is a ligand for IL-18R.

The term "T cell" as used herein is defined as a thymus-derived lymphocyte that participates in a variety of cell-mediated immune reactions.

The term "regulatory T cell" as used herein refers to a $CD4^+CD25^+FoxP3^+$ T cell with suppressive properties. "Treg" is the abbreviation used herein for a regulatory T cell.

The term "helper T cell" as used herein refers to a $CD4^+$ T cell; helper T cells recognize antigen bound to MHC Class II molecules. There are at least two types of helper T cells, Th1 and Th2, which produce different cytokines. Helper T cells become $CD25^+$ when activated, but ronly transiently become $FoxP3^+$.

The term "cytotoxic T cell" as used herein refers to a $CD8^+$ T cell; cytotoxic T cells recognize antigen bound to MHC Class I molecules.

As used herein, "decreasing the number of systemic Tregs" refers to a reduction in the number of systemic Tregs in a subject in response to the administration of IL-18 compared to the number of systemic Tregs in the subject in the absence of the administration of IL-18. The phrase encompasses reducing the number of Tregs to a zero number of detectable cells.

As used herein, "a zero number of detectable cells" refers to any amount of a particular cell type in a subject that cannot be detected by any standard method of cell detection, including, but not limited to, immunophenotype, immunohistochemistry, flow cytometry and polymerase chain reaction.

"Depletion" of a given type of cell, as used herein, refers to reducing or eliminating the function of the cell, rendering the cell ineffective, partially or completely eliminating proliferation of the cell, and/or killing the cell. The term encompasses modulating expression of lineage specific factors, for instance inhibiting expression of FoxP3, thereby altering the cell function. Depletion may be local, for instance, intratumoral, or may be systemic.

A cell type is "selectively depleted" when the cell type is depleted in comparison to another cell type. For instance, administration of IL-18 selectively depletes $CD4^+CD25^+FoxP3^+$ Tregs with respect to $CD4^+$ cells.

As used herein, "administered as part of an allogeneic tissue transplant" refers to administration before, concurrent with, or subsequent to, the transplant of the allogeneic tissue.

As used herein, "IL-18 activity" refers to at least one biological function of IL-18. Non-limiting examples of IL-18 biological functions include induction of IFN-γ in, for instance, PBMCs, induction of NFκB, activation of JNK activity, and binding to IL-18R.

As used herein, "percentage," when used herein to refer to a particular type of T cell means that fraction of the overall T cell population which the particular T cell comprises. Overall T cell population may be quantified by expression of a T cell common antigen. An overall T cell population may also be quantified by quantifying different T cell sub types based on the expression, for instance, of particular cell surface proteins.

It is understood that any and all whole or partial integers between any ranges set forth herein are included herein.

Description

The invention relates to the depletion of Tregs in a subject resulting from the administration of IL-18. Tregs are believed to underlie the failure of an immune response to tumor-associated antigens by suppressing tumor-specific T cells, such as $CD8^+$ T cytotoxic cells, from attacking tumor cells. Similarly, Tregs may reduce the effectiveness of immunotherapy treatments, such as cancer vaccination with tumor-antigen pulsed dendritic cells. Based on the present disclosure, the number of Tregs in a subject with cancer can be specifically depleted by the administration of IL-18. Intratumoral Tregs can be reduced to an undetectable number. The number of circulating Tregs can also be reduced. The percentage of systemic or intratumoral T cells that are Tregs can also be reduced. Similarly, the percentage of systemic or intratumoral T cells that are $CD8^+$ can be increased. Advantageously, overall $CD4^+$ T cell engraftment is not adversely affected by IL-18 administration. Furthermore, $CD8^+$ T cell engraftment is promoted by the administration of IL-18.

Accordingly, the invention provides a method of decreasing the number or percentage of $CD4^+CD25^+FoxP3^+$ Tregs in a subject. IL-18 is administered to the subject which results in the selective depletion of $CD4^+CD25^+FoxP3^+$ Tregs. The invention also provides a method of decreasing the systemic, circulating Tregs in a subject afflicted with cancer, comprising administering a therapeutically-effective amount of IL-18. Similarly, the invention provides a method of decreasing the number of intratumoral Tregs in a subject afflicted with cancer, comprising administering a therapeutically-effective amount of IL-18. Without being bound by theory, it is believed that the depletion of Tregs in a subject with cancer increases the likelihood of an effective immune response mediated, for instance, by tumor-specific $CD8^+$ cytotoxic T cells, being mounted against tumor cells. This is believed because such an immune response will be subjected to reduced or eliminated suppression by Tregs in the method of the invention. Depletion of $CD4^+CD25^+FoxP3^+$ Tregs by IL-18 treatment is also expected to be beneficial for chronic viral infections, for instance retroviral infections.

The invention further provides a method of increasing the number or percentage of $CD8^+$ T cells in a subject afflicted with cancer by administering to the subject a therapeutically-effective amount of IL-18. The $CD8^+$ T cells that are increased may be circulating (that is, systemic) or intratumoral. Without being bound by theory, it is believed increasing the number of $CD8^+$ T cells results in a more effective immune response against a cancer because the number of tumor-specific $CD8^+$ T cells may be increased. Increasing $CD8^+$ T cells is also useful in accelerating recovery of the immune system after marrow depleting or ablation events, including, but not limited to, chemotherapy, radiotherapy and bone marrow transplantation. IL-18 treatment may also permit the administration of a greater amount of or more frequent or longer duration administration of a chemotherapeutic by virtue of preventing or ameliorating T cell depletion caused by the chemotherapeutic. IL-18 treatment to increase $CD8^+$ T cells is also beneficial for recovering immune function in patients experiencing prolonged periods of immunodeficiency, for instance, in patients with HIV infection.

The invention further provides a method of decreasing the number of $CD4^+CD25^+FoxP3^+$ Treg cells in a subject by administering a therapeutically-effective amount of a composition that increases IL-18 activity to the subject. The composition can increase IL-18 activity in a variety of ways, both directly and indirectly. For instance, IL-18 activity is increased by increasing the amount of IL-18. The amount of IL-18 can be increased, for instance, by increasing the expression of endogenous IL-18 or by increasing the processing of IL-18 precursor. Caspase 3 activity results in biologically inactive IL-18. Accordingly, inhibition of caspase 3 activity by administration of a caspase 3 inhibitor will effectively increase IL-18 activity. Caspase 3 inhibitors are known in the art. See, for instance, Han et al., 2002, J. Biol. Chem. 227: 30128-30136; Chu et al., 2005, J. Med. Chem. 48:7637-47; and Okun et al., 2006, J. Biomol. Screen 11:277-85. IL-18 activity may be increased by increasing the half-life of endogenous IL-18 polypeptide or IL-18 mRNA. Alternatively, IL-18 activity may be increased by decreasing the activity of IL-18 binding protein (IL-18BP), which binds and inhibits IL-18. IL-18BP activity may be reduced, for instance, by preventing its binding to IL-18, for instance by a small molecule, or reducing expression of endogenous IL-18BP. The invention is therefore not limited by the manner in which the composition increases IL-18 activity.

The methods of the invention, optionally, further comprise administering at least one additional therapeutic component. Non-limiting examples of therapeutic components include antibodies, antibody-toxin conjugates, chemotherapeutic molecules, DNA vaccines, antisense molecules, siRNA molecules, stem cells, such as hematopoietic stem cells, bone marrow and PBMCs, antigen-presenting cells, such as dendritic cells, and tumor-specific T cells. Chemotherapeutic molecules include any type of agent intended to be toxic to cancer cells. Examples include, but are not limited to, small molecules, radioactive moieties, proteosome inhibitors, steroids, hormones, angiogenesis inhibitors, alkylating agents, antimitotic agents, antimetabolites, plant alkaloids, topoisomerase inhibitors, antitumor antibiotics, radiation, and the like.

Administration of the at least one additional therapeutic component can occur before, concurrent with, or after administration of IL-18 or administration of a composition that increases IL-18 activity. Administration of the at least one additional therapeutic component within about 6 months of IL-18 administration is considered within the scope of the invention. In some embodiments, the at least one additional therapeutic component is administered within about 3 months, within about 1 month, within about 1 day or within about 5 minutes to about 12 hours of IL-18 administration. The schedule of administrating the at least one additional therapeutic component may be the same or different as that for IL-18 or a composition that increases IL-18 activity.

The methods of the invention may be used for any mammal that would benefit from a decrease in $CD4^+CD25^+FoxP3^+$ Treg cells and/or an increase in $CD8^+$ T cells. Preferably, the mammal is a human.

The method of the invention may be used for treatment of any disease or disorder for which a decrease in $CD4^+CD25^+FoxP3^+$ Tregs and/or an increase in $CD8^+$ T cells would provide a therapeutic benefit. Diseases or disorders involving tumors, particularly cancerous tumors, or chronic viral or parasitic infection benefit therapeutically from the depletion of $CD4^+CD25^+FoxP3^+$ Tregs.

More particularly, cancers that may be treated by the methods of the invention include, but are not limited to the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers including, for example, hepatoma, e.g., hepatocellular carcinoma; cholangiocarcinoma; hepatoblastoma; angiosarcoma; hepatocellular adenoma; and hemangioma;

bone cancer including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers including, for example, malignant melanoma, basal cell carcinoma, squamous cell carcinoma, Kaposi's sarcoma, moles dysplastic nevi, lipoma, angioma, dermatofibroma, keloids, and psoriasis;

breast cancers including, for example, ductal carcinoma, lobular carcinoma, inflammatory breast cancer, medullary carcinoma, mucinous (colloid) carcinoma, Paget's disease of the breast, tubular carcinoma, phylloides tumor, metaplastic carcinoma, sarcoma, microcapillary carcinoma and adenoid cystic carcinoma; and adrenal gland cancers including, for example, neuroblastoma.

Cancers may be solid tumors that may or may not be metastatic. Cancers may also occur, as in leukemia, as a diffuse tissue. Thus, the term "tumor cell" as provided herein, includes a cell afflicted by any one of the above identified diseases.

Chronic viral or parasitic infections are also beneficially treated by decreasing CD4$^+$CD25$^+$FoxP3$^+$ Tregs. Non-limiting examples of such infections include retroviral infections, and parasitic infections, including, but not limited to, *Leishmania*, malaria, *Wucheria* sp., *Brugia* sp., *Onchocerca volvulus, Loa boa, Mansonell streptocerca*, and *Dracunculus medinensis*.

IL-18

The IL-18 polypeptide used in the method of the invention can be from any organism. Preferably, to avoid the possibility of antigenicity of a xeno-IL-18 and a resultant anti-xeno-IL-18 immune response and to assure bioactivity, the IL-18 is the same species as the subject to which it is administered. For instance, human IL-18 is preferable in the treatment of humans.

IL-18 genes have been cloned and sequenced in many mammals, including human, mouse (*Mus musculus*), cow (*Bos taurus*), wild boar (*Sus scrofa*), chicken (*Gallus gallus*), rat (*Rattus norvegicus, Sigmodon hispidus*), goat (*Capra hircus*), gerbil (*Meriones unguiculatus*), dog (*Canis familiaris*), cat (*Felis catus*), rhesus monkey (*Macaca mulatta*), sheep (*Ovis aries*) and water buffalo (*Bubalus bubalis*).

In preferred embodiments, IL-18 is human IL-18.

The amino acid sequence of the active form of human IL-18 is YFGKLESKLSVIRNLNDQVLFIDQGNR-PLFEDMTDSDCRDNAPRTIFIISMYKD-SQPRGMAVTISVKCEKISTLSCENKIIS-FKEMNPPDNIKDTKSDIIFFQRSVPGHDNKMQFESSS YEGYFLACEKERDLFKLILKKEDEL-GDRSIMFTVQNED (SEQ ID NO: 1). An exemplary coding sequence for the active form of human IL-18 is tactttg-gcaagcttgaatctaaattatcagtcataagaaatttgaatgaccaagttctcttcatt gaccaaggaaatcggcctctatttgaagatatgactgattctgactgtagagataatg caccccggaccatatttattataagtatgtataaagatagccagcctagaggtatggc tgtaactatactgtgaagtgtgagaaaatttcaactctctcctgtgagaacaaaatta tttcctitaaggaaatgaatcctcctgataacatcaaggatacaaaaagtgacatcat attctttcagagaagtgtcccaggacatgataataagatgcaatttgaatcttcatcat acgaaggatactttctagcttgtgaaaaagagagagaccantaaactcattttgaaa aaagaggatgaattgggggatagatctataatgttcactgttcaaaacgaagac (SEQ ID NO: 2). The amino acid sequence of the active form of murine IL-18 is NFGRLHCTTAVIRNINDQVLFVD-KRQPVFEDMTDIDQSASEPQTRLIIYMYKDSEVRGLA VTLSVKDSKMSTLSCKNKIISFEEMDPPENIDDIQSDL IFFQKRVPGHNKMEFESSLYEGHFLACQKEDDAFKLI LKKKDENGDKSVMFTLTNLHQS (SEQ ID NO: 3). An exemplary coding sequence for the active form of murine IL-18 is aactttggccgacttcactgtacaaccgcagtaatacggaatataaa tgaccaagttctatcgttgacaaaagacagcctgtgttcgaggatatgactgatattg atcaaagtgccagtgaaccccagaccagactgataatatacatgtacaaagacag tgaagtaagaggactggctgtgaccctctctgtgaaggatagtaaaatgtctaccct ctcctgtaagaacaagatcatttcctttgaggaaatggatccacctgaaaatattgat gatatacaaagtgatctcatattctttcagaaacgtgttccaggacacaacaagatg gagtttgaatcttcactgtatgaaggacactttatgcttgccaaaaggaagatgatgc tttcaaactcattctgaaaaaaaaggatgaaaatggggataaatctgtaatgttcact ctcactaacttacatcaaagt (SEQ ID NO: 4).

IL-18 polypeptides useful in the invention may also have modifications. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are IL-18 polypeptides that have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The IL-18 polypeptides useful in the invention may further be conjugated to non-amino acid moieties that are useful in their therapeutic application. In particular, moieties that improve the stability, biological half-life, water solubility, and immunologic characteristics of the peptide are useful. A non-limiting example of such a moiety is polyethylene glycol (PEG).

Covalent attachment of biologically active compounds to water-soluble polymers is one method for alteration and control of biodistribution, pharmacokinetics, and often, toxicity for these compounds (Duncan et al., 1984, Adv. Polym. Sci. 57:53-101). Many water-soluble polymers have been used to achieve these effects, such as poly(sialic acid), dextran, poly (N-(2-hydroxypropyl)methacrylamide) (PHPMA), poly(N-vinylpyrrolidone) (PVP), poly(vinyl alcohol) (PVA), poly (ethylene glycol-co-propylene glycol), poly(N-acryloyl morpholine (PAcM), and poly(ethylene glycol) (PEG) (Powell, 1980, Polyethylene glycol. In R. L. Davidson (Ed.) HANDBOOK OF WATER SOLUBLE GUMS AND RESINS. McGraw-Hill, New York, chapter 18). PEG possess an ideal set of properties: very low toxicity (Pang, 1993, J. Am.

Coll. Toxicol. 12: 429-456) excellent solubility in aqueous solution (Powell, supra), low immunogenicity and antigenicity (Dreborg et al., 1990, Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p 145-154; Olson et al., 1997, Preparation and characterization of poly(ethylene glycol)ylated human growth hormone antagonist. In J. M. Harris and S. Zalipsky (Eds) Poly(ethylene glycol): Chemistry and Biological Applications. American Chemical Society, Washington, D.C., p 170-181). Exemplary PEGylated IL-18 molecules are disclosed in WO 2004/091517 (corresponding to U.S. Pat. Publication No. 2005000861), each of which is incorporated herein by reference in its entirety; use of any of these PEGylated IL-18 is envisioned in the methods of the invention.

The IL-18 polypeptides useful in the method of the invention may be prepared by chemical or biological means. Biological methods include, without limitation, purification from a biological sample having endogenous IL-18 production, expression of a nucleic acid encoding an IL-18 polypeptide in a host cell and in vitro translation systems.

To ensure that the polypeptide obtained from either chemical or biological synthetic techniques is the desired polypeptide, analysis of the peptide composition can be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use in the method of the invention, the IL-18 polypeptide is purified to remove contaminants. In this regard, it will be appreciated that the peptide will be purified so as to meet the standards set out by the appropriate regulatory agencies. Any one of a number of conventional purification procedures may be used to attain the required level of purity. An exemplary method for obtaining purified, active IL-18 for use in the instant invention is disclosed in WO 2001/98455 (corresponding to U.S. Pat. Publication No. 20030143198), which are each herein incorporated by reference in its entirety.

In preparing a substantially pure polypeptide, an immunological, enzymatic or other assay can be used to monitor purification at each stage in the procedure. Protein purification methods are well known in the art, and are described, for example in Deutscher et al. (ed., 1990, *Guide to Protein Purification*, Harcourt Brace Jovanovich, San Diego, Calif.).

Administration, Dosing and Dosing Schedule

Administration of IL-18 in a method of the invention can be achieved in a number of different ways, using methods known in the art. Such methods include, but are not limited to, providing exogenous IL-18 protein to a subject, expressing a recombinant IL-18 gene, upregulating expression of an endogenous IL-18 gene, increasing the half-life or stability of IL-18 mRNA, increasing the translation of IL-18 mRNA, downregulating expression of IL-18BP, and/or inhibiting the binding of IL-18BP to IL-18.

In a preferred embodiment, exogenous IL-18 is administered to a subject. The exogenous IL-18 protein may be identical in sequence to the endogenous IL-18 protein or may be a different sequence. The exogenous protein may also be a hybrid or fusion protein to facilitate distinguishing it from endogenous IL-18 or to facilitate delivery to target cells. For instance, a hybrid IL-18 protein may comprise a tumor-specific targeting sequence.

Upregulating expression of an endogenous IL-18 gene can be achieved by any method known in the art. For instance, the IL-18 gene promoter can be genetically modified to increase transcription. Constitutive and inducible promoters are well-known in the art, as are means for genetic modification. Upregulating expression of IL-18 gene expression can also be accomplished indirectly by upregulating expression of IL-18 gene-specific transcriptional activator proteins in cells that express an endogenous IL-18 gene. Upregulating expression of IL-18 is preferably accompanied by an increase in caspase-1 (ICE) activity by means known to the skilled artisan. Caspase-1 is responsible for processing biologically-active IL-18 precursor in vivo to yield biologically-active IL-18.

Cells expressing an endogenous IL-18 gene can be targeted for in vivo genetic modification. Alternatively, cells may be isolated, genetically modified ex vivo and then administered to the subject, thereby achieving IL-18 administration. The genomic structure and promoter of human IL-18 gene is known (Gracie et al., 2003, J. Leukocyte Biol. 73:213-224; el Kares et al., 2000, Arch. Inst. Pasteur Tunis 77(1-4):55-58). The IL-18 gene has two promoters, a constitutive promoter and a promoter inducible by LPS and IFNγ.

Expression vectors and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.Y.), and in Ausubel et al. (eds, 2005, Current Protocols in Molecular Biology, John Wiley & Sons, New York, N.Y.). Any expression vector compatible with the expression of IL-18 is suitable for use in the instant invention, and can be selected from the group consisting of a plasmid DNA, a viral vector, and a mammalian vector. The expression vector, or a vector that is co-introduced with the expression vector, can further comprise a marker gene. Marker genes are useful, for instance, to monitor transfection efficiencies. Marker genes include: genes for selectable markers, including but not limited to, G418, hygromycin, and methotrexate, and genes for detectable markers, including, but not limited to, luciferase and GFP. The expression vector can further comprise an integration signal sequence which facilitates integration of the isolated polynucleotide into the genome of a target cell.

Molecules that upregulate endogenous IL-18 gene expression, upregulate endogenous IL-18 gene-specific transcriptional activator proteins, downregulate expression of IL-18BP, inhibit binding of IL-18BP to IL-18, increase the half-life and/or stability of IL-18 polypeptide and/or IL-18 mRNA, increase the translation of IL-18 mRNA, or increase the processing of the pro-IL-18 polypeptide to form active IL-18 can be readily identified by methods known to the skilled artisan.

Compounds that may be tested for desired activity may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145).

Examples of methods for the synthesis of molecular libraries may be found in the art, for example, in: DeWitt et al., 1993, Proc. Natl. Acad. Sci. USA 90:6909-6913; Erb et al., 1994, Proc. Natl. Acad. Sci. USA 91:11422-11426; Zuckermann et al., 1994, J. Med. Chem. 37:2678-2685; Cho et al., 1992, Science 261:1303-1305; Carell et al., 1994, Angew. Chem. Int. Ed. Engl. 33:2059-2061; Carell et al., 1994, Angew. Chem. Int. Ed. Engl. 33:2061-2064; and Gallop et al., 1994, J. Med. Chem. 37:1233-1251.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869), or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

The therapeutic methods of the invention thus encompass the use of pharmaceutical compositions of an appropriate small molecule, protein or peptide and/or isolated nucleic acid to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 $\mu$M and 10 $\mu$M in a mammal.

Typically, dosages which may be administered in a method of the invention to an animal, preferably a human, range in amount from 0.5 $\mu$g to about 50 mg per kilogram of body weight of the animal. The precise dosage administered will vary depending upon any number of factors, including but not limited to, the type of animal and type of disease state being treated, the age of the animal and the route of administration. Preferably, the dosage of the compound will vary from about 1 $\mu$g to about 10 mg per kilogram of body weight of the animal. More preferably, the dosage will vary from about 3 $\mu$g to about 1 mg per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals including commercially relevant mammals, such as non-human primates, cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parenterally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in *Remington's Pharmaceutical Sciences* (1985, Genaro, ed., Mack Publishing Co., Easton, Pa.), which is incorporated herein by reference.

EXAMPLES

The invention is now described with reference to the following Examples. These Examples are provided for the purpose of illustration only, and the invention is not limited to these Examples, but rather encompasses all variations which are evident as a result of the teachings provided herein.

Experimental Example 1

IL-18 Treatment of Tumor-Bearing Mice $\beta$2-microglobulin$^{null}$/NOD/scid mice were injected subcutaneously with a lung adenocarcinoma cell line (L55). After tumors were established (100-200 mm$^3$), the mice were injected intraperitoneally with $50 \times 10^6$ human peripheral blood mononuclear cells (PBMCs), followed by a three week course of daily subcutaneous (s.c.) injections of 0.75 mg/kg recombinant human IL-18 (rhIL-18) in 6 mice and mock-rhIL-18 treatment in 4 mice. Tumor volumes were monitored, and upon sacrifice (24 hours after the final rhIL-18 injection), the intratumoral distribution and number of human T cell subsets was determined by immunohistochemistry. Paraffin sections from the tumor were reacted with an antibody specific for human CD45 (FIG. 1, left panel), human CD8 (FIG. 1, middle panel), or human CD4 (FIG. 1, right panel).

As shown in FIG. 1, the overall level of human CD45+ cell engraftment was increased (left panel) in IL-18 treated mice (black bars), compared to mock-treated mice (open bars). IL-18 injections also increased the infiltration of tumors by CD8$^+$ human T cells (middle panel) but not CD4$^+$ human T cells (right panel). This increase was entirely due to an increase in the number of CD8$^+$ T cells. No increase in the number of CD4$^+$ T cells was observed.

TABLE 1

| rhIL-18 | CD45$^+$ | | | | CD3$^+$CD4$^+$ | | | | CD3$^+$CD8$^+$ | | | |
|---|---|---|---|---|---|---|---|---|---|---|---|---|
| | PB† | PC‡ | Lvr$^a$ | Spl$^b$ | PB | PC | Lvr | Spl | PB | PC | Lvr | Spl |
| (−) | 13.2 | 4.3 | 9.2 | 53.1 | 6.0 | 3.1 | 4.4 | 23.0 | 7.8 | 0.8 | 3.8 | 18.5 |
| | ±4.7 | ±0.3 | ±1.0 | ±5.3 | ±2.5 | ±0.7 | ±0.5 | ±2.9 | ±3.2 | ±0.1 | ±0.4 | ±1.4 |
| (+) | 27.9 | 4.3 | 11.1 | 106.7 | 10.5 | 4.3 | 4.1 | 33.5 | 5.0 | 0.9 | 7.6 | 60.1 |
| | ±11.8 | ±0.3 | ±0.5 | ±13.2 | ±2.7 | ±0.4 | ±1.2 | ±11.3 | ±0.2 | ±0.1 | ±0.1* | ±0.1* |

Values are represented as averages +/− S.E.M.
†PB: peripheral blood
‡PC: Peritoneal cavity
$^a$Lvr: Liver
$^b$Spl: Spleen
*indicates a significant difference (p < 0.02) between control and rhIL-18-treated mice The effect of human IL-18 on systemic T cell distribution was examined by injecting non-tumor-bearing $\beta_2$-microglobulin$^{−/−}$ NOD/SCID mice with 50 million human PBMCs. Twenty-four hours later, a three week course of daily rhIL-18 injections (0.75 mg/kg) or mock rhIL-18 injections was initiated. Table 1 summarizes the absolute counts ($\times 10^6$) of human CD45$^+$, CD3$^+$CD4$^+$ and CD3$^+$CD8$^+$ recovered following sacrifice of the mice. rhIL-18 increased the number of human CD8$^+$ T cells in the spleen and liver. In contrast, the number of CD8$^+$ T cells did not increase in the peripheral blood or peritoneal cavity in response to rhIL-18 administration. Notably, rhIL-18 injection had no effect on the overall engraftment levels or localization of CD4$^+$ T cells.

Figure 2:
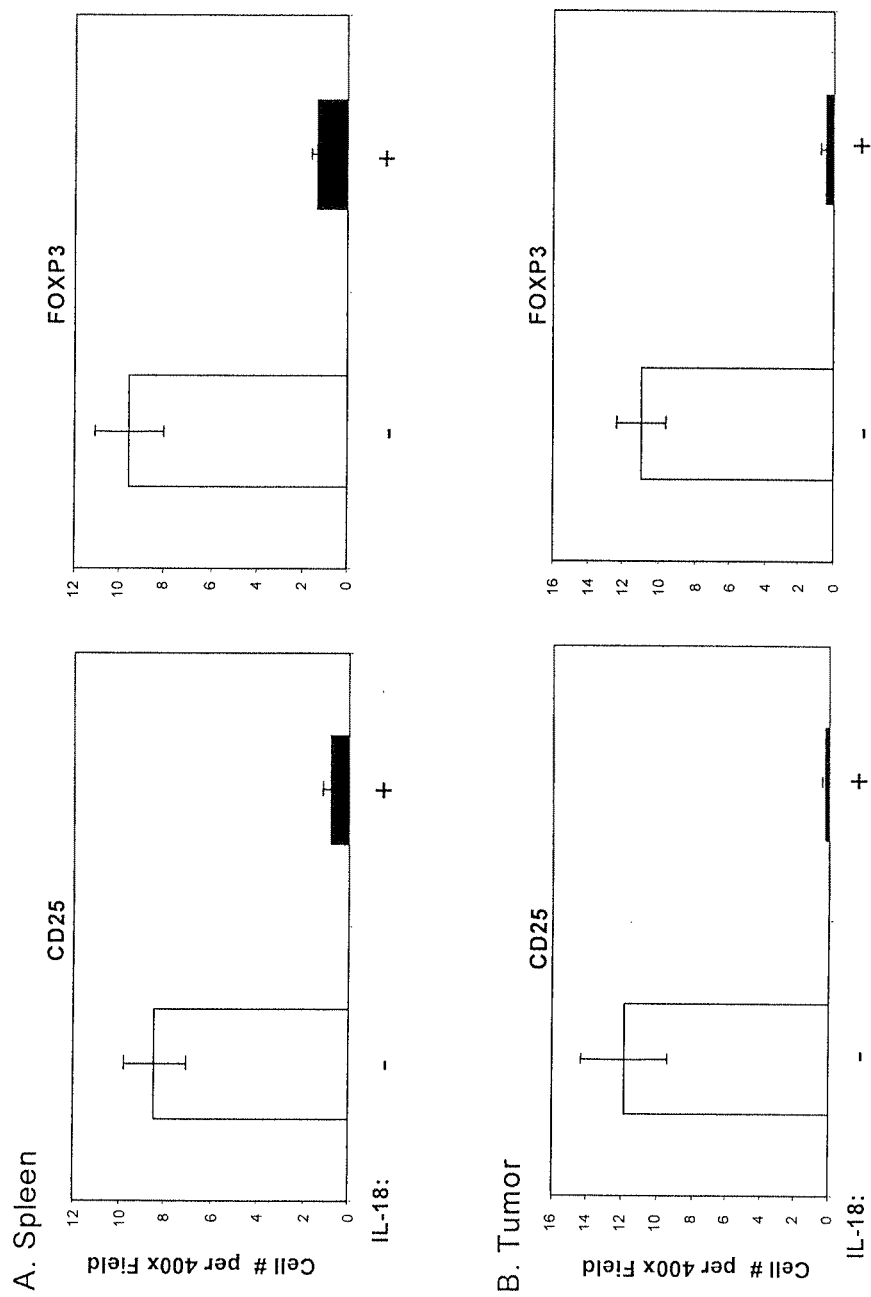
FIG. 2, comprising

Although rhIL-18 treatment did not result in overall changes in the number or distribution of human CD4$^+$ cells, it did result in a substantial decrease in the overall number of CD4$^+$CD25$^+$FoxP3$^+$ regulatory T cells (Tregs). Tumor-bearing mice were injected subcutaneously with $5 \times 10^7$ allogeneic human PBMCs, followed by a three week course of daily subcutaneous injections of rhIL-18. The animals were then sacrificed, and paraffin sections of tumor and spleen were prepared. The sections were reacted with antibodies specific for human CD4, human CD25, or human FoxP3. As shown in FIG. 2, rhIL-18 treatment resulted in a marked diminution in the number of Tregs in both tumor (FIG. 2B) and spleen (FIG. 2A).

Experimental Example 2

IL-18 Treatment of Non-Tumor-Bearing Mice $\beta$2-microglobulin$^{null}$/NOD/scid mice (n=6) were injected intraperitoneally (i.p.) with 50×10$^6$ human PBMCs, followed by a three week course of daily subcutaneous injection of 0.75 mg/kg rhIL-18. IL-18 injections began 24 hours after the PBMC injection. After the three week course of IL-18 injections, the animals were sacrificed. Peripheral blood and fluid from the peritoneal cavity were obtained and processed for flow cytometry. In addition, the liver and the spleen were isolated from the animals. Portions of the organs were fixed, embedded in paraffin, and sectioned for immunohistochemical analysis. The remainder of the organs were processed for flow cytometry. Antibodies specific for human CD45, CD4, CD8, CD25, or FoxP3 were used in both immunohistochemical and flow cytometric analyses. In some experiments, the distribution of cells of human origin in other organs, including the lungs, kidney, skin and bone marrow was examined.

Figure 3:
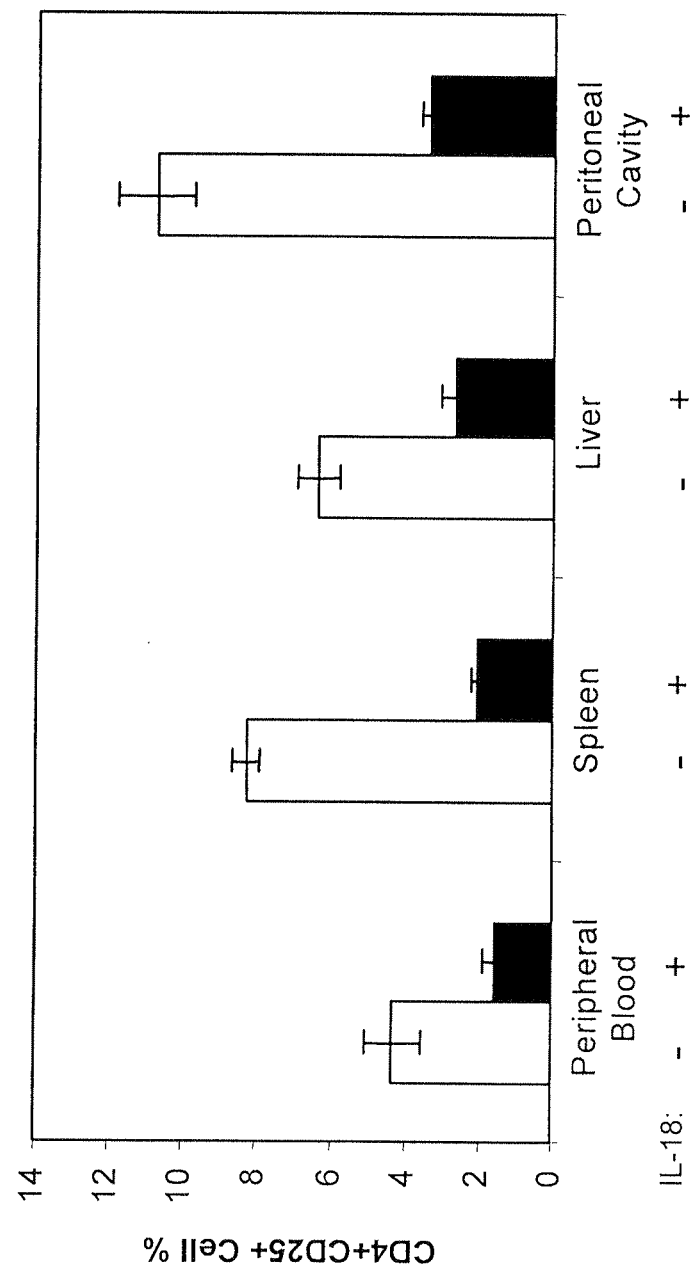
FIG. 3 depicts a bar graph of measurements of $CD4^+$ CD25+ T cells in various tissues in non-tumor-bearing rhIL-18-treated $\beta$2-microglobulin$^{-/-}$/NOD/scid mice. Cells were stained with antibodies to human CD45, CD4, and CD25 and analyzed by flow cytometry. The percentage of $CD4^+CD25^+$ cells was determined by first gating on $CD45^+$ cells. Filled bars represent values obtained in IL-18-treated animals; open bars represent values obtained in mock-treated animals.

FIG. 3 depicts the flow cytometry data measuring Tregs in the peripheral blood, peritoneal cavity, spleen, and liver. The number of Tregs is markedly reduced in mice treated with IL-18 compared to mice that were mock-treated.

Figure 4:
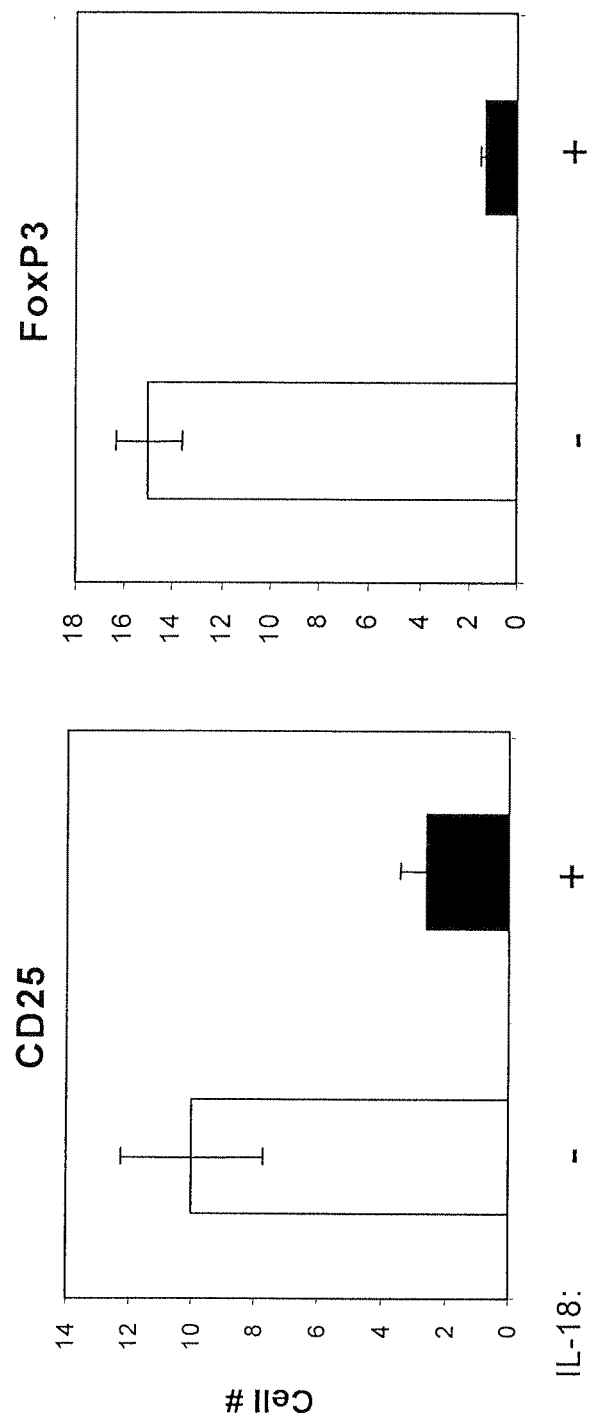
FIG. 4 is a series of two bar graphs depicting the number of Tregs in IL-18 treated $\beta$2-microglobulin$^{-/-}$/NOD/scid mice without tumors. Antibody-reactive cells per 400× field were enumerated blindly. Solid bars depict sections from IL-18-treated animals, while open bars represent sections from mock-IL-18-treated animals.

Tregs in the spleen were quantified by immunohistochemistry. The data is shown in FIG. 4. These data also indicate that IL-18 treatment resulted in marked reduced numbers of Tregs. Thus, the IL-18-mediated reduction in Tregs observed does not require the presence of a tumor.

The data described herein demonstrate that human IL-18 treatment results in marked alterations in the composition and distribution of human T cells. The most profound difference is the dramatic decrease in the number of CD4$^+$CD25$^+$ FoxP3$^+$ Treg cells. This decrease appears to be systemic and is not dependent on the presence of an allogeneic human tumor. IL-18 treatment also increased the number of CD8$^+$ T cells, both intratumorally and systemically. Thus, IL-18 treatment can be used to modulate the composition and distribution of T cells in vivo.

Experimental Example 3

IL-18 Treatment of Non-Tumor-Bearing Mice Injected with PBMCs or PBLs $\beta$2-microglobulin$^{-/-}$/NOD/scid mice were injected intraperitoneally with 50×10$^6$ human PBMCs or 30×10$^6$ human peripheral blood lymphocytes (PBLs), followed by a three week course of daily subcutaneous (s.c.) injections of 0.75 mg/kg rhIL-18. After the three week course of IL-18, the animals were sacrificed. The spleen was isolated from each animal, fixed, embedded in paraffin and sectioned for immunohistochemical analysis. Paraffin sections from the spleen were reacted with antibodies specific for human FoxP3 or human CD8.

Figure 5:
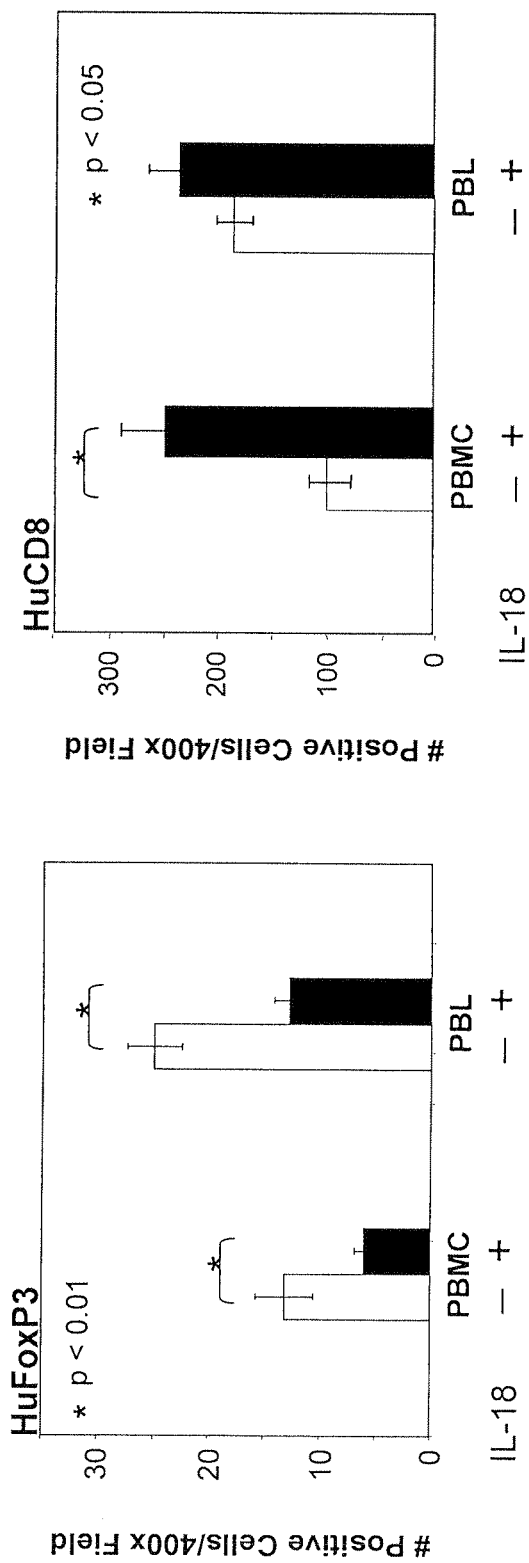
FIG. 5 is a series of two bar graphs depicting the number of Tregs in IL-18 treated $\beta$2-microglobulin$^{-/-}$/NOD/scid mice without tumors injected with either human peripheral blood mononuclear cells (PMBC) or human peripheral blood lymphocytes (PBL). Paraffin sections of spleen were reacted with antibodies specific for human FoxP3 (left graph) or human CD8 (right graph). Antibody-reactive cells per 400× field were enumerated blindly. Solid bars depict sections from IL-18-treated animals, while open bars represent sections from mock-IL-18-treated animals.

The results are depicted in FIG. 5. A statistically-significant decrease in Tregs occurs both with injection of PBMCs and of PBLs (left graph). However, a statistically-significant increase in CD8+ T cells occurs only with the injection of PBMCs (right graph). Therefore, the results demonstrate that the IL-18-mediated increase in CD8$^+$ T cells is dependent on the presence of monocyte/macrophages. In contrast, the IL-18-mediated decrease in Tregs is independent of the presence of monocyte/macrophages.

Experimental Example 4

IL-18 Treatment of Different Strain of Non-Tumor-Bearing Mice

Treg-depleted human PBMCs were prepared by passing human PBMCs over columns (Miltenyi) that were calibrated to remove CD25-high cells, thereby removing Tregs. NOD/scid/$\gamma_c^{null}$ (NOG) mice were injected intraperitoneally with 20×10$^6$ Treg-depleted human PBMCs supplemented with either 4×10$^6$ autologous CD4$^+$ T cells (left panel) or 4×10$^6$ autologous Tregs (middle and right panels). A group of NOG mice receiving Treg-depleted PBMCs and autologous Tregs received daily s.c. injections of 0.75 mg/kg rhIL-18 for three weeks. Human cell engraftment in the peripheral blood was monitored 14, 28, and 36 days post-injection, and the number of CD8$^+$ T cells/μl peripheral blood was determined.

Figure 6:
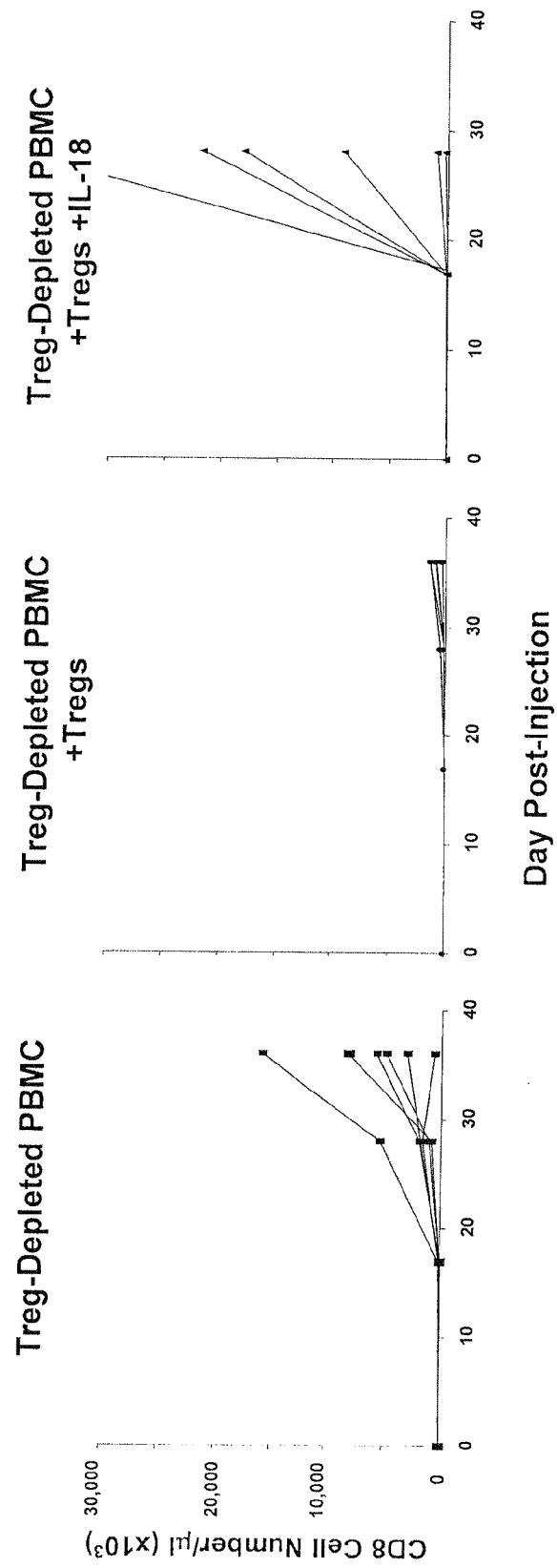
FIG. 6 is a series of graphs depicting data for NOD/scid/ $\gamma_c^{null}$ mice injected with PBMCs as indicated above each graph. Human cell engraftment in the peripheral blood was monitored 14, 28 and 36 days post-injection.

The results are depicted in FIG. 6. Comparison of the left panel (mice administered Treg-depleted PBMCs) and middle panel (mice administered Treg-depleted PBMCs supplemented with Tregs) demonstrates that addition of Tregs decreased peripheral blood CD8$^+$ T cell numbers. However, daily IL-18 administration prevented the Treg-mediated suppressive effect (right panel). In fact, human T cell proliferation was so robust in the IL-18-treated animals that graft-versus-host disease symptoms became evident around day 28, necessitating the sacrifice of the animals in this group.

This experiment also demonstrates that the suppressive effect of rhIL-18 on human Treg activity was observed in two different strains of immune-deficient mice. Accordingly, the activity of human IL-18 on human Tregs is independent of the mouse model.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treatment comprising:
   administering a therapeutically-effective amount of interleukin 18 (IL-18) to a subject in need thereof,
   detecting the level of CD4$^+$CD25$^+$FoxP3$^+$ Tregs in the subject, wherein the level of CD4$^+$CD25$^+$FoxP3$^+$ Tregs is reduced as compared to the level of Tregs in the subject prior to treatment; and
   administering a second therapeutic.

2. The method of claim 1, wherein said level of Tregs is reduced to a zero number of detectable cells.

3. The method of claim 1, wherein said IL-18 is human IL-18.

4. The method of claim 1, wherein said subject is a human subject.

5. The method of claim 4, wherein said human subject is afflicted with at least one disorder selected from cancer, a retroviral infection or a parasitic infection.

6. The method of claim 5, wherein said cancer is lung cancer, gastrointestinal cancer, genitourinary tract cancer, liver cancer, bone cancer, nervous system cancer, gynecological cancer, breast cancer, hematologic cancer, skin cancer, or adrenal gland cancers.

7. The method of claim 6, wherein the cancer is lung cancer.

8. The method according to claim 1, wherein said subject is afflicted with cancer.

9. A method according to claim 8, wherein the Treg cells are systemic or intratumoral.

10. The method of claim 1, wherein said second therapeutic component is an antibody, an antibody-toxin conjugate, a toxin, a chemotherapeutic molecule, a DNA vaccine, an antisense molecule, an siRNA molecule, a stem cell, a tumor-specific T cell, or an antigen-presenting cell.

11. The method of claim 1, wherein said IL-18 is administered as part of an allogeneic tissue transplant.

12. The method of claim 11, wherein said tissue transplant is selected from peripheral blood mononuclear cell (PBMC) transplant or bone marrow transplant (BMT).

13. The method of claim 1, wherein said IL-18 is conjugated to polyethylene glycol (PEG).

14. The method of claim 1, wherein the IL-18 is administered prior to administration of a second therapeutic.

15. The method of claim 1, wherein the IL-18 is administered after vaccination with tumor-antigen pulsed dendritic cells.

16. The method of claim 1, wherein the IL-18 is administered intratumorally.

17. A method for treating a subject afflicted with lung adenocarcinoma, said method comprising
   administering a therapeutically-effective amount of IL-18 to said subject, and
   detecting the level of CD4$^+$CD25$^+$FoxP3$^+$ Tregs in the subject, wherein the number of Treg cells is decreased in said subject as compared to the level of Tregs in the subject prior to treatment.

18. The method of claim 17, wherein the IL-18 is administered prior to administration of a second therapeutic.

* * * * *